US00PP08338P

United States Patent [19]

de Ruiter

[11] Patent Number: Plant 8,338

[45] Date of Patent: Aug. 10, 1993

[54] MINIATURE ROSE PLANT NAMED RUINIDAN

[75] Inventor: Gijsbert de Ruiter, Hazerswoude, Netherlands

[73] Assignee: De Ruiter's Nieuwe Rozen B.V., Hazerswoude, Netherlands

[21] Appl. No.: 904,517

[22] Filed: Jun. 25, 1992

[51] Int. Cl.[5] ..... A01H 5/00

[52] U.S. Cl. ..... Plt./9

[58] Field of Search ..... Plt./7.1, 9

[56] References Cited

U.S. PATENT DOCUMENTS

P.P. 6,243 8/1988 de Ruiter ..... Plt. 9

P.P. 6,875 6/1989 Marciel ..... Plt. 9

*Primary Examiner*—Howard J. Locker

*Attorney, Agent, or Firm*—Christie, Parker & Hale

[57] ABSTRACT

A new variety of miniature rose plant having pink flowers produced on a good pot forcing plant also suitable for growing outdoors in gardens.

2 Drawing Sheets

SUMMARY OF THE INVENTION

The present invention relates to a new and distinct variety of rose plant of the miniature rose class, which was originated by me by crossing as the seed and pollen parents unnamed and unpatented seedlings of my creation. The varietal denomination of the new variety is 'Ruinidan'.

Among the novel characteristics possessed by this new variety which distinguishes it from its parent and all other varieties of which I am aware are its pink flowers borne on a plant particularly suited for production of flowering pot plants and for growing in outdoor gardens. The new variety can be reproduced through propagation by cuttings, grafting, budding, and micropropagation. Flowers of the new variety are long lasting on the plant. Asexual reproduction by budding, grafting and propagation of cuttings of the new variety as performed in Hazerswoude, Holland, shows that the foregoing and other distinguishing characteristics come true to form and are established and transmitted through succeeding propagations.

BRIEF DESCRIPTION OF ILLUSTRATION

The accompanying illustrations show typical specimens of the vegetative growth and flowers of the new variety in different stages of development depicted in color as nearly true as it is reasonably possible to make the same in a color illustration of this character. Phenotypic expression, including colors, may vary depending upon growing conditions, such as under different climate, soil, and cultivation conditions.

One accompanying illustration is of a plant of the new variety of miniature rose showing flowering and growth habit; but the colors depicted are not true. The other illustration shows details of the new miniature rose variety illustrated in colors believed to more accurately depict flower coloration.

The other illustration shows details of the new variety. In the illustration there is shown the top of a young shoot, 1; compound three and five leaflet leaves, 2 and 3, respectively; a stem, 5; buds, 6 and 7; a flower, 8, about one-half open; and a flower 9, fully open. Also shown are flower stems 10, 11 and 12, with reproductive organs.

DETAILED DESCRIPTION OF THE NEW VARIETY

The following is a detailed description of my new variety, with color terminology in accordance with The Royal Horticultural Society Colour Chart (R.H.S.C.C.) and horticultural terminology in accordance with standard terminology used in UPOV-approved horticultural guidelines. The terminology used in color descriptions herein refers to plate numbers in the aforementioned color chart.

Parentage: Seedling.

*Seed parent.*—Unnamed seedling.

*Pollen parent.*—Unnamed seedling.

Class: Miniature.

As can be seen in the accompanying illustrations, one illustration shows one sample of flowering plant of the new variety depicting the pot plant habit of growth and flowering. Since flowering is nearly continuous, this floriferous variety can remain attractively in bloom for long periods when given proper care and culture.

The following further horticultural observations were made of specimens grown under glass in Holland.

FLOWER

Blooming habit: Nearly continuous.

A. Bud:

(1) *Size.*—Medium.

(2) *Form.*—Ovate (before separation of sepals); urn shaped after sepals part.

(3) *Color.*—As sepals divide, bud color is near 55A.

(4) *Sepals.*—Longer than bud, simple to slightly foliated.

(5) *Peduncle.*—Length — medium to long for miniature. Aspect — straight. Strength — erect. Color — medium green.

B. Bloom: Flower: Medium size for miniature; viewed from above — round; viewed from side, (a) upper part of fully opened flower, flat; (b) lower part of fully opened flower, flat.

(1) *Size.*—Average size when fully expanded — about 5 cm.

(2) *Borne.*—Primarily singly, one to a stem.

(3) *Form.*—Ovoid becoming flat; outer petals roll under.

(4) *Petalage.*—About 31 under normal conditions — semi-double.

(5) *Color.*—After sepals separate and part and petals being to unfurl, color is from near to 55C to 55B; petals' top surface tends to be deeper toned at center where petals bunch; reverse surface tends to be similar to top surface. Coloring at point of petal attachment is near 155C. Overall tonality from a distance is attractive pink.

(6) *Pedicel.*—Very few hairs or prickles.

(7) *Fragrance.*—Slight.

C. Petals:

(1) *Texture.*—Very good substance.

(2) *Appearance.*—Inside velvety and outside satiny.

(3) *Form and size.*—Medium for miniature, obovate.

(4) *Arrangement.*—Regularly arranged, imbricated.

(5) *Petaloids in center.*—Few.

(6) *Lasting quality.*—Long lasting quality on plant.

REPRODUCTIVE ORGANS

A. Stamens, filaments and anthers:

*Arrangement and Color.*—Regularly arranged around styles; color filaments — yellow to yellow green.

B. Pollen:

*Color.*—Pale yellow.

C. Styles: Short, white generally not hairy.

D. Stigmas: Positioned above anthers.

E. Hips: Very small, pitcher-shaped.

PLANT

A. Form: Upright to bushy.

B. Growth: Vigorous, average height about 15 cm.

C. Foliage: Compound 3, and 5 leaflets (1) *Size.*—Medium for a miniature.

(2) *Quantity.*—Abundant.

(3) *Color.*—Foliage at time of first flowering — light green.

(4) *Shape.*—Oval, pointed.

(5) *Texture.*—Upper side is weak glossy; underside is matte.

(6) *Edge.*—Serrate.

(7) *Serration.*—Ordinary, acuminate apices.

(8) *Leaf stem.*—Color — medium green.

(9) *Stipules.*—Ordinary, medium to long, medium green, distinct auricle

(10) *Leaflets.*—Cross section — slight concave, little or no undulation at margin; terminal leaflet (blade) — long, narrow, obtuse base; petiole — short.

D. Wood:

(1) *New wood.*—Color — light to medium green with slight bronze cast, little or no anthocyanin coloration.

(2) *Old wood.*—Color — medium green.

E. Prickles (Thorns):

(1) *Prickles.*—Present, quantity (main stalk) — ordinary; On laterals from stalk — ordinary; Form — straight; Shape of upper side — flat Shape of lower side — deep concave; Length — about 5 min; Color — tan to pale pink; Position — irregular.

I claim:

1. A new and distinct variety of rose plant of the miniature rose class, substantially as shown and described.

* * * * *

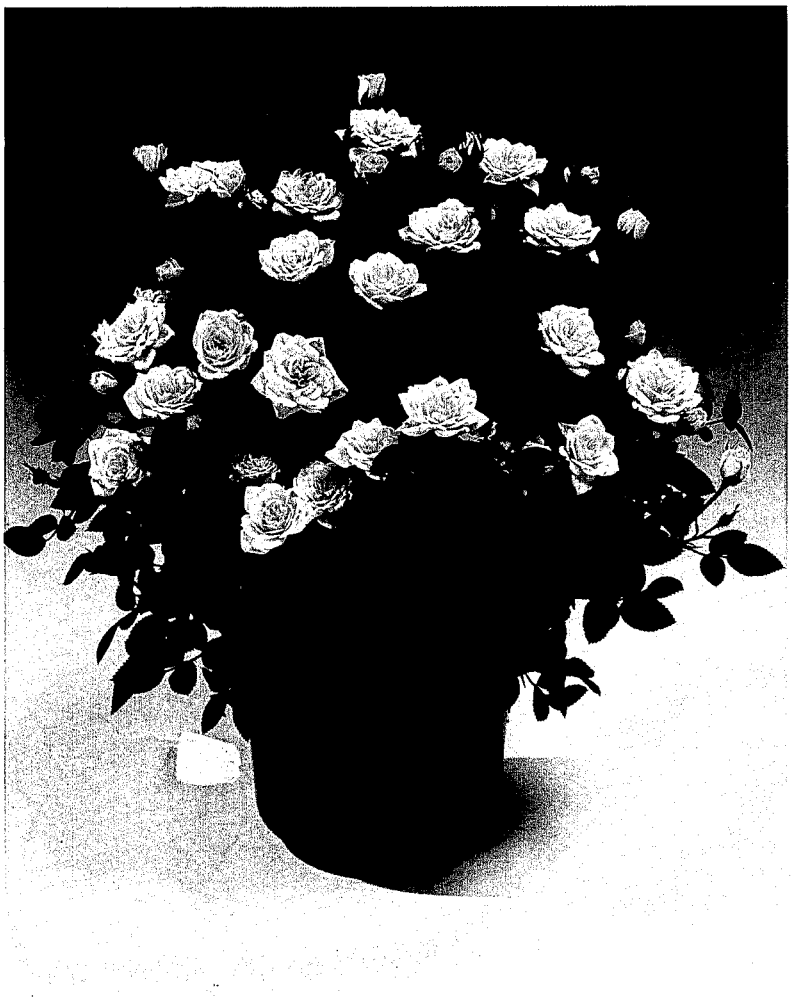

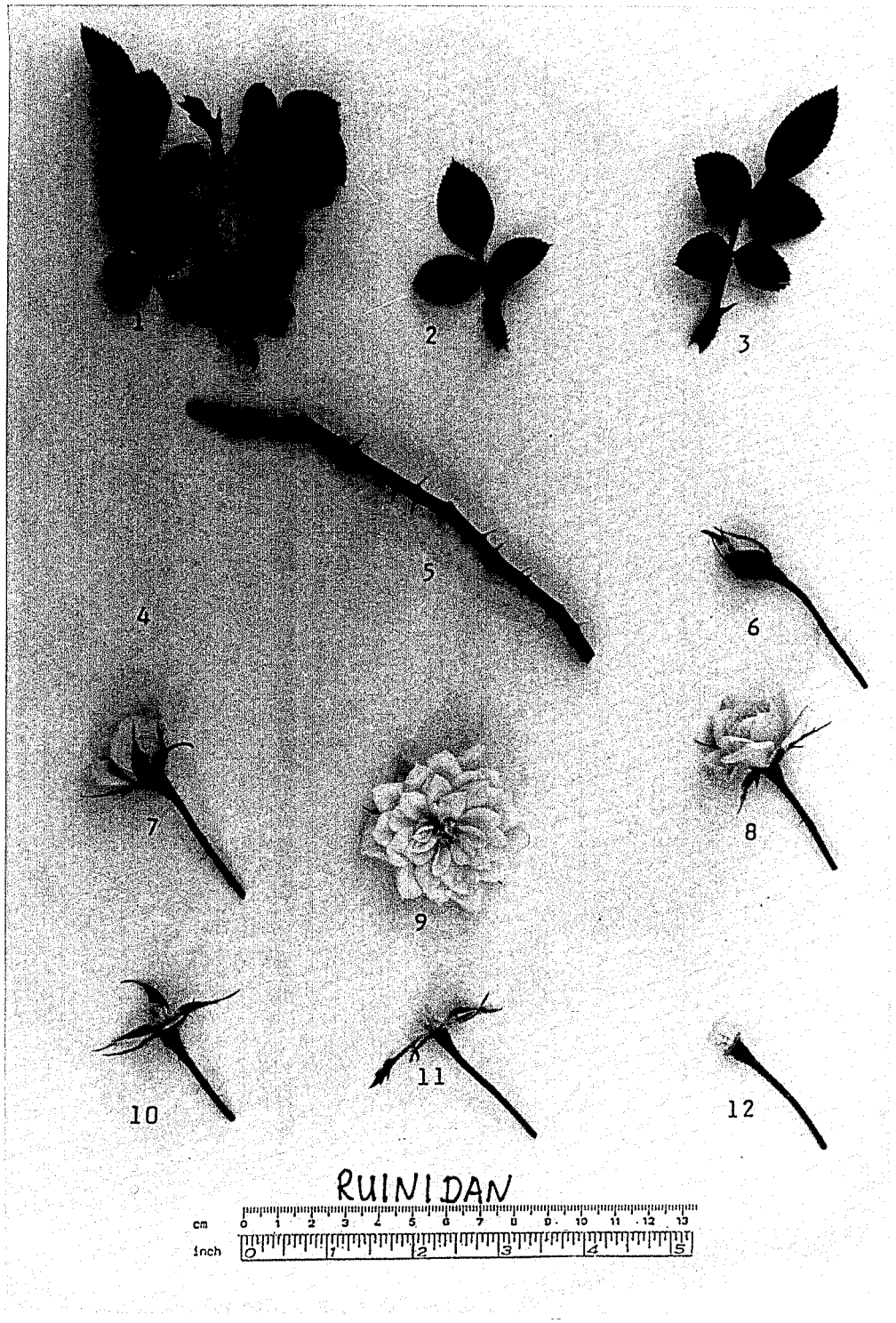
1
2
3
4
5
6
7
8
9
10
11
12
RUINIDAN
cm
inch

UNITED STATES PATENT AND TRADEMARK OFFICE

CERTIFICATE OF CORRECTION

PATENT NO. : Plant 8,338

DATED : August 10, 1993

INVENTOR(S) : Gijsbert de Ruiter

It is certified that error appears in the above-indentified patent and that said Letters Patent is hereby corrected as shown below:

Column 1, line 24, change "BRIEF DESCRIPTION OF ILLUSTRATION" to -- BRIEF DESCRIPTION OF ILLUSTRATIONS --.

Column 1, Lines 40-46, move the paragraph beginning with "The other illustration..." to Column 2 and insert between lines 23 and 24.

Column 4, line 29, change "min" to -- mm --.

Signed and Sealed this

Twenty-first Day of June, 1994

*Attest:*

BRUCE LEHMAN

*Attesting Officer*

*Commissioner of Patents and Trademarks*